(12) United States Patent
Zhe et al.

(10) Patent No.: US 10,386,249 B2
(45) Date of Patent: Aug. 20, 2019

(54) WEARABLE INDUCTIVE-FORCE SENSOR

(71) Applicants: Jiang Zhe, Copley, OH (US); Li Du, Akron, OH (US)

(72) Inventors: Jiang Zhe, Copley, OH (US); Li Du, Akron, OH (US)

(73) Assignee: The University of Akron, Akron, OH (US)

( * ) Notice: Subject to any disclaimer, the term of this patent is extended or adjusted under 35 U.S.C. 154(b) by 129 days.

(21) Appl. No.: 14/627,494

(22) Filed: Feb. 20, 2015

(65) Prior Publication Data

US 2015/0233776 A1    Aug. 20, 2015

Related U.S. Application Data

(60) Provisional application No. 61/942,310, filed on Feb. 20, 2014.

(51) Int. Cl.
| | |
|---|---|
| *H02J 7/00* | (2006.01) |
| *G01L 1/14* | (2006.01) |
| *A61B 5/103* | (2006.01) |
| *A61B 5/00* | (2006.01) |
| *A61B 5/05* | (2006.01) |
| *A61B 5/053* | (2006.01) |

(52) U.S. Cl.
CPC ............ *G01L 1/146* (2013.01); *A61B 5/05* (2013.01); *A61B 5/053* (2013.01); *A61B 5/1038* (2013.01); *A61B 5/6807* (2013.01); *A61B 2562/164* (2013.01)

(58) Field of Classification Search
CPC .......... G01L 1/146; A61B 5/05; A61B 5/053; A61B 5/1038; A61B 5/6807; A61B 2562/164; A61B 5/062; A61B 5/746; H02J 7/025

USPC .............. 600/300, 301, 587, 592; 73/862.69
See application file for complete search history.

(56) References Cited

U.S. PATENT DOCUMENTS

| | | | | |
|---|---|---|---|---|
| 2004/0261544 | A1* | 12/2004 | Peshkin .................... | G01L 1/14 73/862.53 |
| 2006/0021261 | A1* | 2/2006 | Face ........................ | A43B 3/00 36/132 |
| 2008/0203144 | A1* | 8/2008 | Kim ......................... | A61B 5/00 235/105 |
| 2010/0259217 | A1* | 10/2010 | Baarman ................. | H02J 5/005 320/108 |
| 2012/0325019 | A1* | 12/2012 | Shau .................... | A61B 5/1036 73/862.59 |

* cited by examiner

*Primary Examiner* — May A Abouelela
(74) *Attorney, Agent, or Firm* — Renner Kenner Greive Bobak Taylor and Weber; Tim Hodgkiss; Ray Weber

(57) ABSTRACT

A wearable inductive-force sensor, which provides high-sensitivity dynamic measurements of both normal force and shear force, utilizes three spiral planar force sensing coils. These spiral planar coils allow the measurement of shear force in the x and y directions and the measurement of a normal force in the z direction. The force sensor is configured to be mounted in various locations, such as an insole of a shoe, so as to provide real-time force sensing of forces that are applied to a patient's feet as they move. In addition, force-measurement electronics used with the force sensor are configured to use resonance-frequency division signal multiplexing to monitor the response of the force sensing coils, which allows the sensor to have minimal complexity, while still being highly sensitive.

16 Claims, 8 Drawing Sheets

WEARABLE INDUCTIVE-FORCE SENSOR

CROSS-REFERENCE TO RELATED APPLICATION

This application claims the benefit of U.S. Provisional Application No. 61/942,310 filed Feb. 20, 2014, the contents of which are incorporated herein by reference.

TECHNICAL FIELD

Generally, the present invention relates to force sensors. Particularly, the present invention relates to inductive-force sensors configured to measure a normal force and a shear force in two-directions. More particularly, the present invention relates to a wearable inductive-force sensor for an insole of a shoe that is used to measure forces applied a person's feet for medical diagnostic purposes.

BACKGROUND OF THE INVENTION

Most diabetic patients, due to the complications of their disease, suffer from nerve damage or neuropathy in their extremities, such as their feet, which results in a loss of tactile sensation. This loss of tactile sensation can lead to the formation of ulcers or open wounds in the layers of skin of a patient's feet. Recently, it has been determined that such foot ulcers are related to the application of normal forces and shear forces on the plantar portion or bottom surface of the patient's foot.

As such, a variety of measurement systems have been developed in an attempt to detect the forces that are applied to a diabetic's feet, in real-time, using load sensors and pressure sensors. For example, the F-Scan® system and Pedar® system, which use pressure-sensor arrays, have been used to measure the pressure distribution on a person's feet. The disadvantage of these force-measurement systems is that while they are sensitive to normal forces, they are insensitive to shear forces. Other sensor-array devices have also been developed, which are able to detect normal forces and shear forces simultaneously. However, such sensor-array devices are bulky in size, making its attachment to a patient's feet impractical. In addition, compact sensors have also been developed, which overcomes these drawbacks and integrates two shear sensors and an F-Scan® pressure sensor distribution sensor into an insole of a shoe. However, due to the complexity of its design, such a device is extremely high in cost, and therefore many diabetic patients who could benefit from a wearable force monitoring device are unable to afford its cost.

Therefore, there is a need for a miniature inductive-force sensor for dynamic, simultaneous measurement of normal and shear forces that are applied to a diabetic's feet, which is low cost. In addition, there is a need for a miniature inductive-force sensor that is configured to provide real-time monitoring of normal and shear forces that are applied to a person's feet. Furthermore, there is a need for a miniature inductive-force sensor that is configured to be mounted on or integrated into in an insole of a shoe. Additionally, there is a need for a miniature inductive-force sensor that is capable of simultaneous measurement of normal force and two-axis shear force using only one set of measurement circuitry, thereby making the inductive-force sensor compact in size.

SUMMARY OF THE INVENTION

In light of the foregoing, it is a first aspect of the present invention to provide a force sensor comprising a substrate; a first, second and third coil disposed on the substrate, the coils electrically coupled in series; a capacitor coupled in parallel with each one of the plurality of coils; a flexible section disposed on the plurality of coils; and a rigid section disposed on the flexible section, the rigid section being formed of conductive material, such that the flexible section allows the rigid section to move relative to the coils; wherein the flexible section has at least two edges, such that one edge passes through the center of the first coil and another edge passes through the center of the second coil, and the third coil is disposed between the flexible section and the substrate, such that the coils detect a change in impedance based on the movement of the rigid section relative to the coils.

BRIEF DESCRIPTION OF THE DRAWINGS

These and other features and advantages of the present invention will become better understood with regard to the following description, appended claims, and accompanying drawings wherein:

DETAILED DESCRIPTION OF THE INVENTION

An inductive-force sensor is generally referred to by numeral 10, as shown in FIG. 1 of the drawings. The force sensor 10 comprises a plurality of spiral-wound force sensing coils 20. For example, in one embodiment three sensing coils 20A-C, as discussed herein, may be used, however any suitable number of coils 20 may be utilized. Each sensing coil 20A-C comprises a multi-turn spiral planar coil that is made of suitable magnet wire. In one embodiment, each of the three sensing coils 20 comprises a 30-turn spiral planar coil, having an inner diameter of about 1 mm and an outer diameter of about 7 mm, which is made of AWG 34 magnet wire having a diameter of about 200 um. However, it should be appreciated that each coil 20A-C may also comprise a coil having any suitable number of turns and any suitable diameter, and may be formed of any other suitable magnet wire of any suitable diameter. It should also be appreciated that the sensor 10 may be configured whereby one of the coils 20A-C may comprise a number of turns and/or magnet wire that is different from one or more of the other coils 20A-C, or all of the coils 20A-C may be configured with the same physical characteristics.

Figure 4:
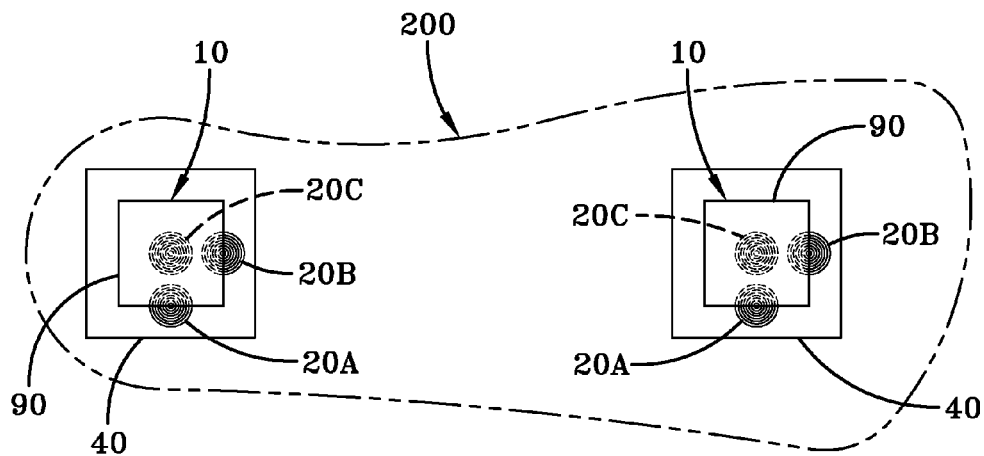
FIG. 4 is a top plan view of the wearable inductive force-sensor incorporated into an insole of a shoe in accordance with the concepts of the present invention.

The sensing coils 20 have opposed inner (i.e. bottom) and outer (i.e. top) surfaces 30 and 34, such that the inner surface 30 of the coils 20A-C is mounted or attached to a substrate 40 using any suitable means of fixation, such as adhesive for example. The substrate 40 may be formed of any suitable dielectric or electrically non-conductive material, such as plastic for example. In one aspect, the substrate 40 may be formed of a rigid material that can support the weight of an individual. In another aspect, the substrate 40 may comprise an insole 200, as shown in FIG. 4, which is to be placed and worn on the inside of a shoe. As such, when a patient who is being monitored by the sensor 10, such as a diabetic patient, wears shoes including the insole 200, the forces applied to their feet as they perform any physical activities, such as running or walking can be identified by one or more sensors 10 that may be used.

Figure 1A:
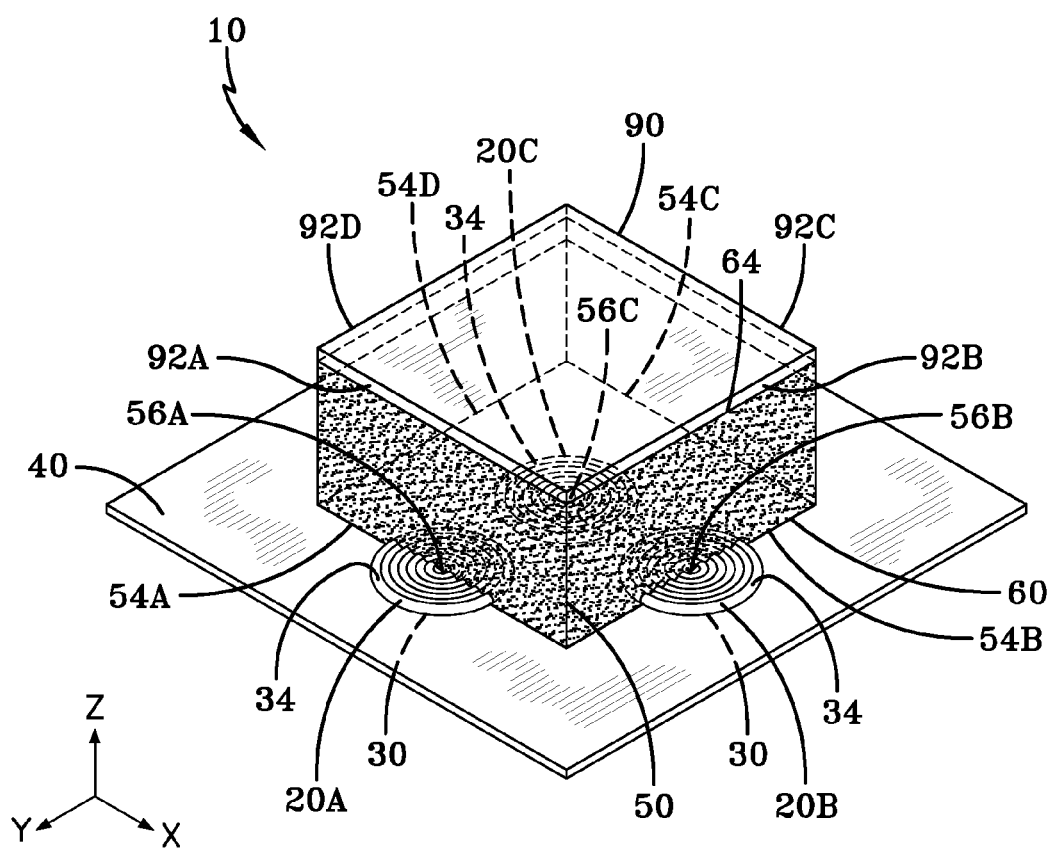
FIG. 1A is a perspective view of a wearable inductive-force sensor in accordance with the concepts of the present invention.

The sensor 10 also includes a flexible section or block 50 having opposed inner (i.e. bottom) and outer (i.e. top) surfaces 60 and 64. As such, the inner surface 60 of the flexible section 50 is disposed upon the substrate 40 so that the outer surface 34 of the coils 20A-C are in physical contact with the inner surface 60 of the flexible section 50, as shown in FIG. 1A. In addition, the flexible section 50 comprises a substantially square-shaped block. In one aspect, the flexible section 50 may comprise a shape having a dimension of 25.4 mm in length, 25.4 mm in width and 12.7 mm in thickness for example, although the flexible section may take on any other suitable dimension/shape. As such, the edges 54A-D that bound the flexible section 50 that are proximate to the inner surface 60 of the flexible section have the same length dimension. As such, the edges 54A and 54B of the flexible section 50 are configured so as to pass through the center 56A and 56B of each of the coils 20A and 20B, while coil 20C is completely covered by the flexible section 50, as shown in FIG. 1. That is, the coil 20C is sandwiched entirely between the flexible section 50 and the substrate 40. In one aspect, the center 56A of the coil 20A is positioned at the center of the edge 54A of the flexible section 50, while the center 56B of the coil 20B is positioned at the center of the edge 54B of the flexible section 50. As such, coils 20A and 20B have substantially half of their surface area (i.e. top surface 34) covered by a conductive member 90 disposed on the flexible section 50, while the remaining half is not covered by the conductive member 90 and is left exposed. It should be appreciated that the substrate 40 may be attached to the flexible section 50 using any suitable means of fixation. In addition, the flexible section 50 may be formed of rubber, such as neoprene rubber, or any other suitable flexible material. It should also be appreciated that the flexible section 50 may comprise any suitable dimension or shape. In addition, the flexible section 50 is configured to be suitably resilient, so as to be compressed/stretched when force is applied thereto, but return to its initial position upon the removal of the applied force.

Disposed on the outer surface 64 of the flexible section 50 is the conductive member 90. The conductive member 90 comprises a substantially planar plate that is formed of any suitable conductive material, such as stainless steel for example. In one embodiment, the conductive member 90 is formed of a rigid material, so as not to deform under the weight of the individual or patient using the sensor 10. In addition, the conductive member 90 is bounded by edges 92A-D, which are substantially aligned with respective edges 56A-D of the flexible section 50. As such, the conductive member 90 is aligned with the coils 20A-C, such that the edges 92A and 92B of the conductive member 90 are aligned with, and pass through, the respective centers 56A and 56B of the coils 20A and 20B. In one aspect, the center 56A of the coil 20A is positioned at the center of the edge 92A of the conductive member 90, while the center 56B of the coil 20B is positioned at the center of the edge 92B of the conductive member 90. In addition, coil 20C is positioned relative to the conductive member 90, such that the center 56C of the coil 20 C is aligned with the center of the conductive member 90. The conductive member 90 may be attached to the flexible section 50 using any suitable means of fixation, such as silicone adhesive for example. As such, during operation of the sensor 10, pressure is applied to the conductive member 90 by a patient placing his or her weight (i.e. foot) thereon. Thus, the movement of the conductive member 90 relative to the sensing coils 20A-C, which is enabled by the flexibility of the flexible section 50, allows the sensor 10 to detect the forces applied to a patient's feet in a manner to be discussed.

Figure 1B:
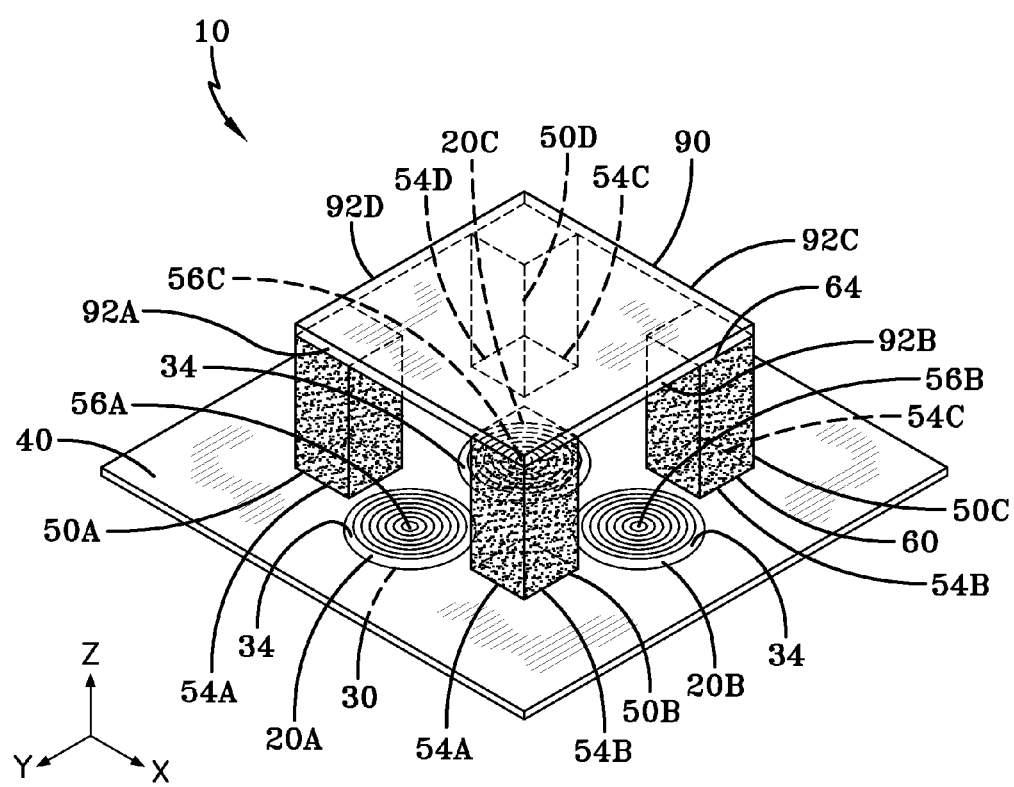
FIG. 1B is a perspective view of an alternative wearable inductive-force sensor in accordance with the concepts of the present invention.

In another embodiment, shown in FIG. 1B, the sensor 10 may be configured, such that the flexible section 50 comprises discrete flexible members 50A-D, such as pillars, which are disposed at the corners of the conductive member 90. As such, the flexible members 50A-D are positioned so that they are not in contact with the sensing coils 20A-C. However, any number of flexible members 50A-D may be used in any particular configuration or arrangement in order to support the conductive member 90 above the coils 20A-C, so long as the relationship between the edges 92A-B of the conductive member 90 and the centers 56A-B of the sensing coils 20A-B; and the relationship between the center 56C of sensing coil 20C and the center of the conductive member 90 is provided, as previously discussed with regard to FIG. 1A.

Figure 1C:
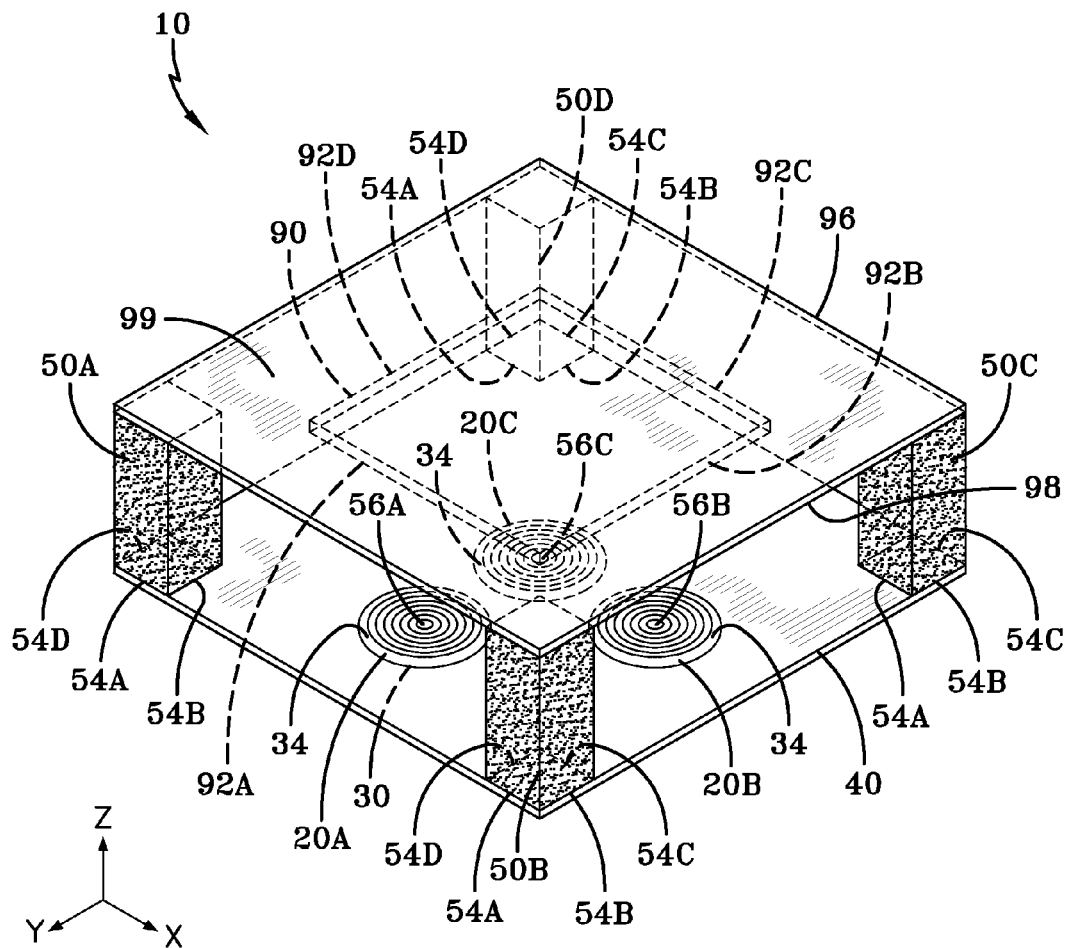
FIG. 1C is a perspective view of another alternative wearable inductive-force sensor in accordance with the concepts of the present invention.

In still another embodiment, similar to that discussed with respect to FIG. 1B, a cover plate 96 may be disposed upon the discrete flexible members 50A-D, as shown in FIG. 1C. This cover plate 96 is formed of any suitable dielectric material, such as plastic for example. The cover plate 96 includes an inner and outer surface 98 and 99, such that the conductive member 90 is carried on the inner surface 98 or outer surface 99 of the cover plate 96. In one aspect, the cover plate 96 may be formed of a flexible material or rigid material, which is also able to accommodate the weight of an individual. As such, in this embodiment, the conductive member 90 is not directly supported by the flexible members 50A-D, but rather the flexible members 50A-D indirectly support the conductive member 90 via the cover plate 96. It should also be appreciated that any number of flexible members 50A-D may be used in any particular configuration or arrangement in order to support the cover plate 96 and the conductive member 90 above the coils 20A-C, so long as the relationship between the edges 92A-B of the conductive member 90 and the centers 56A-B of the sensing coils 20A-B; and the relationship between the center 56C of sensing coil 20C and the center of the conductive member 90 is provided, as previously discussed with regard to FIG. 1A.

It should be appreciated that any number of sensors 10 may be attached or integrated into the insole 40 of the shoe, as shown in FIG. 4, to provide a dynamic force measurement of the entire foot or any portion thereof.

Figure 2:
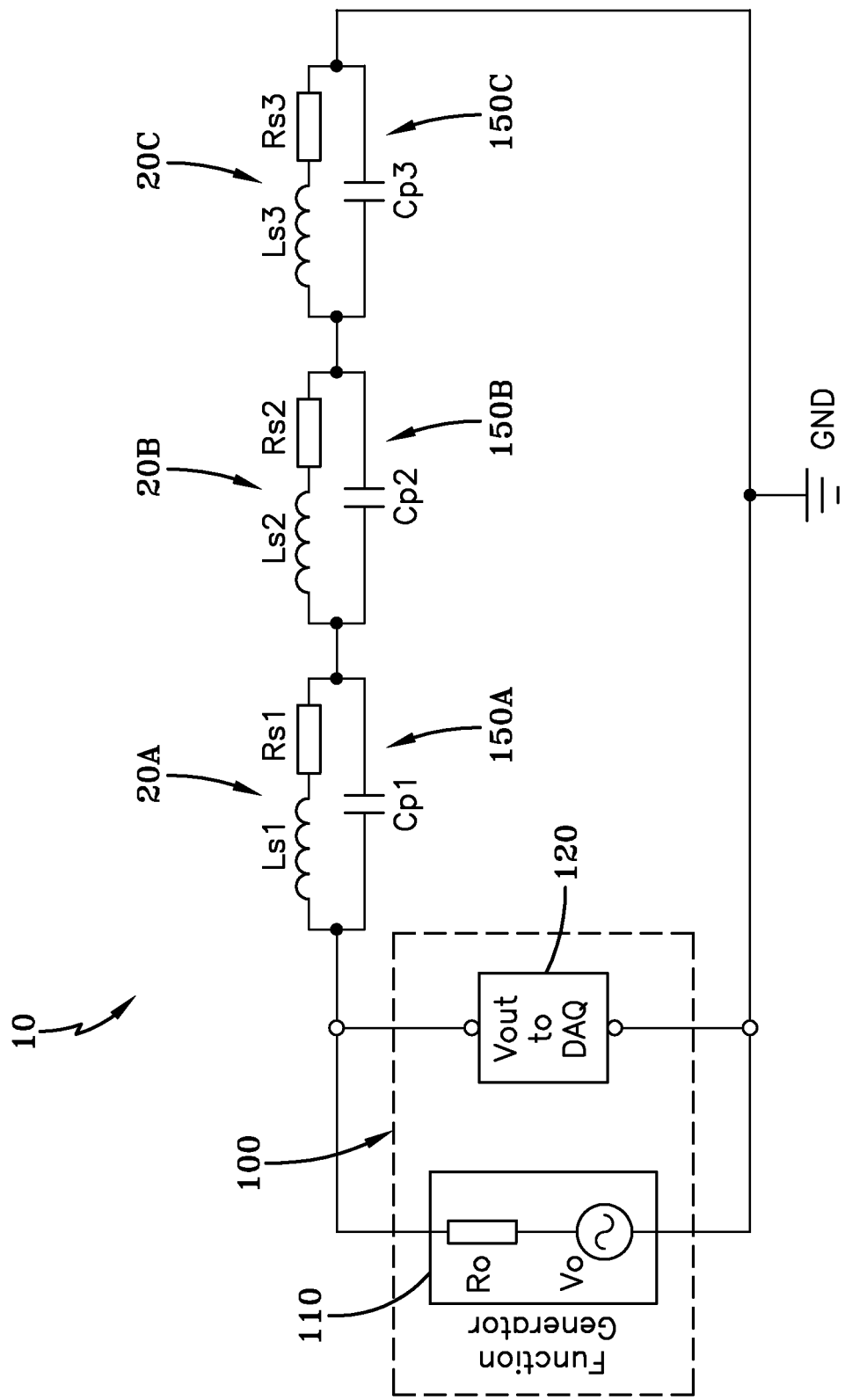
FIG. 2 is a schematic view of the wearable inductive force-sensor interfaced with a force-measurement device in accordance with the concepts of the present invention.

In order to place the inductive-force sensor 10 into operation, it is interfaced with a force-measurement device 100, as shown in FIG. 2. The force-measurement device 100 includes a signal or function generator 110, which includes a signal source $V_o$ that is configured to generate an A.C. (alternating current) signal $V_o$, which is applied to the coils 20A-C. In series with the signal source $V_o$ is a resistance $R_o$. The force-measurement device 100 also includes a force data-acquisition (DAR) unit 120 that is configured to detect and record the response of the coils 20A-C when a force is applied to the inductive-force sensor 10 in a manner to be discussed. It should be appreciated that the force-measurement device 100 may be embodied in hardware software, or a combination of both to carry out the functions to be discussed. In one aspect, the force-measurement device 100 may comprise a portable computing unit that is configured to be worn on the user's shoe, which is capable of recording and storing the force data that is acquired by the sensor 10 as it is being worn by an individual. This force data can then be transferred, using any suitable wired or wireless communication interface 102, such as a wired USB interface or a wireless WIFI/BLUETOOTH interface, for example, to a remote computer system for further analysis.

In particular, the signal generator 110 and resistance $R_o$, which may be any suitable resistance value, are coupled in series with each of the series-coupled coils 20A-C, while the data-acquisition unit 120 is coupled in parallel across the coils 20A-C to measure a voltage $V_{out}$. It should be appreciated that the data-acquisition unit 120 comprises any suitable data-acquisition computing system, which may be implemented in hardware, software or a combination of both, that is capable of measuring, storing and analyzing $V_{out}$ that is generated by the response of the sensing coils 20A-B during operation of the sensor 10.

The sensing coils 20A-C, as shown in FIG. 2, are each represented by an inductance that is denoted by $L_{si}$ and a resistance denoted by $R_{si}$, where i=1, 2, 3 identifies the resistive and inductive component that is associated with each respective coil 20A-C. That is, $L_{si}$ and $R_{si}$ represent the series inductance and resistance of each sensing coil 20A-C. In addition, each sensing coil 20A-C is electrically connected in parallel with a respective external capacitor $C_{pi}$, where i=1, 2, 3. As such, each coil 20A-C defines a respective parallel LC resonant circuit 150A-C, which is formed from the combination of $L_{si}$, $R_{si}$ and $C_{pi}$ Furthermore, each parallel LC resonant circuit 150A-C has a unique resonant frequency.

During operation of the sensor 10, the A.C. signal generator 110 of the force-measurement device 100 applies an A.C. signal $V_o$ to each of the coils 20A-C, which causes the coils 20A-C to each generate a magnetic field. In addition, an eddy current is induced inside the conductive plate 90, which generates a magnetic field that is opposite to the original magnetic field generated by the coils 20A-C. As a result, the total magnetic flux is decreased, which leads to a decrease in the inductance $L_s$ of each coil 20A-C. Thus, the smaller the distance between the coils 20A-C and the conductive plate 90, denoted as $Z_d$ (i.e. normal force), the larger the eddy current that is induced and, therefore, the larger the drop in the inductance $L_s$ experienced by the coils. Similarly, a larger area of the conductive plate 90 covers the coils 20A-C (e.g., a larger $X_d$ or $Y_d$ shear force) will also result in a larger induced eddy current, which causes a decrease in the inductance $L_s$. That is, when shear forces are applied to the sensor 10, more of the total surface area (i.e. top surface 34) of the coils 20A and 20B becomes covered by the conductive plate 90.

Figure 3A:
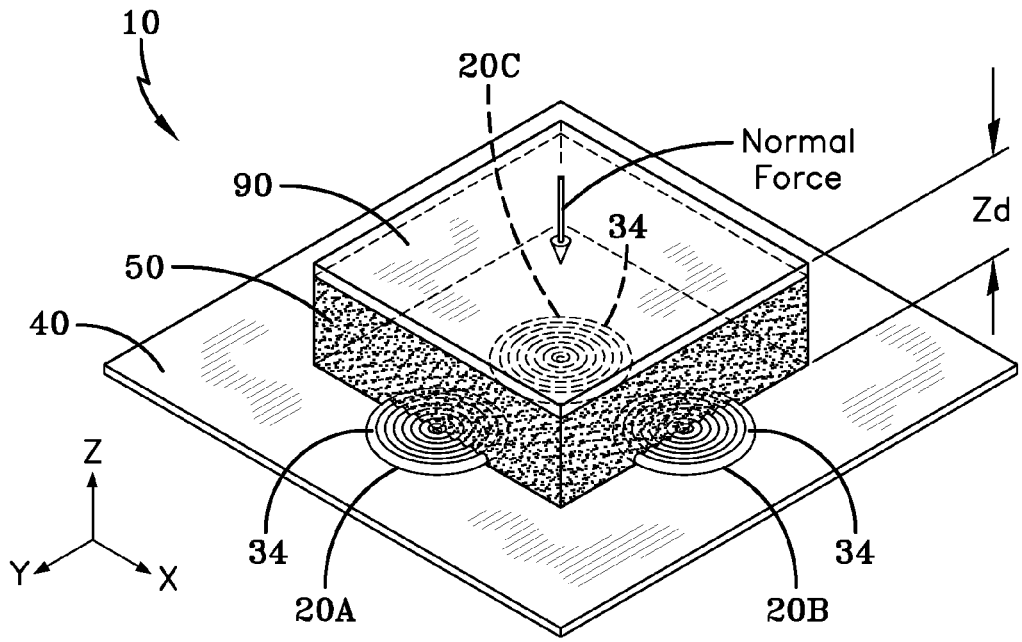
FIG. 3A is a perspective view of the wearable inductive force-sensor when a normal force is applied thereto in accordance with the concepts of the present invention.
Figure 3B:
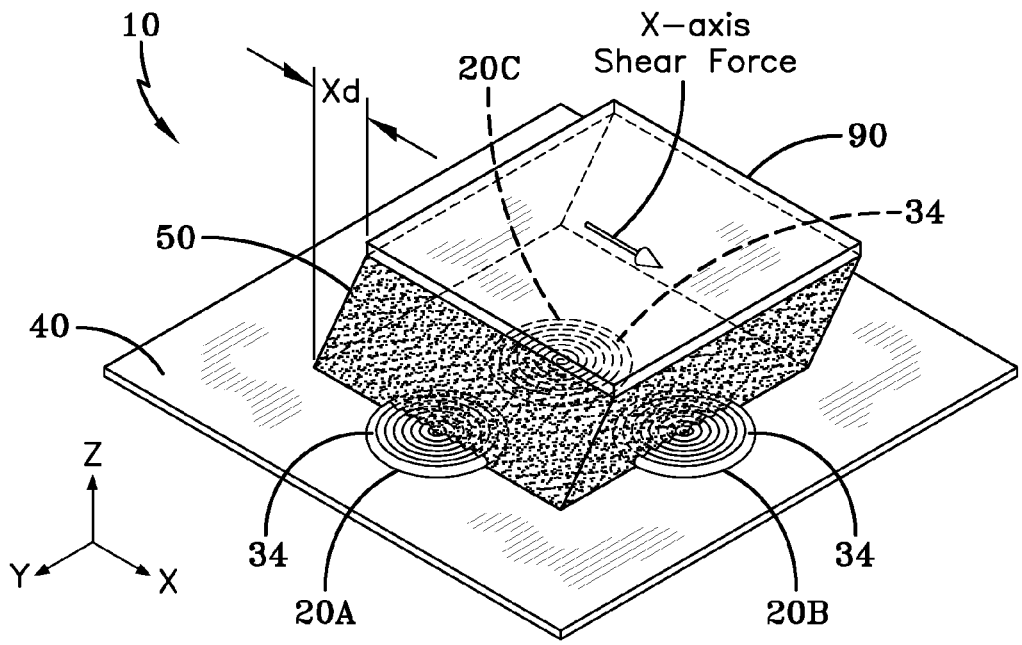
FIG. 3B is a perspective view of the wearable inductive force-sensor when a shear force is applied thereto along the x-axis in accordance with the concepts of the present invention.
Figure 3C:
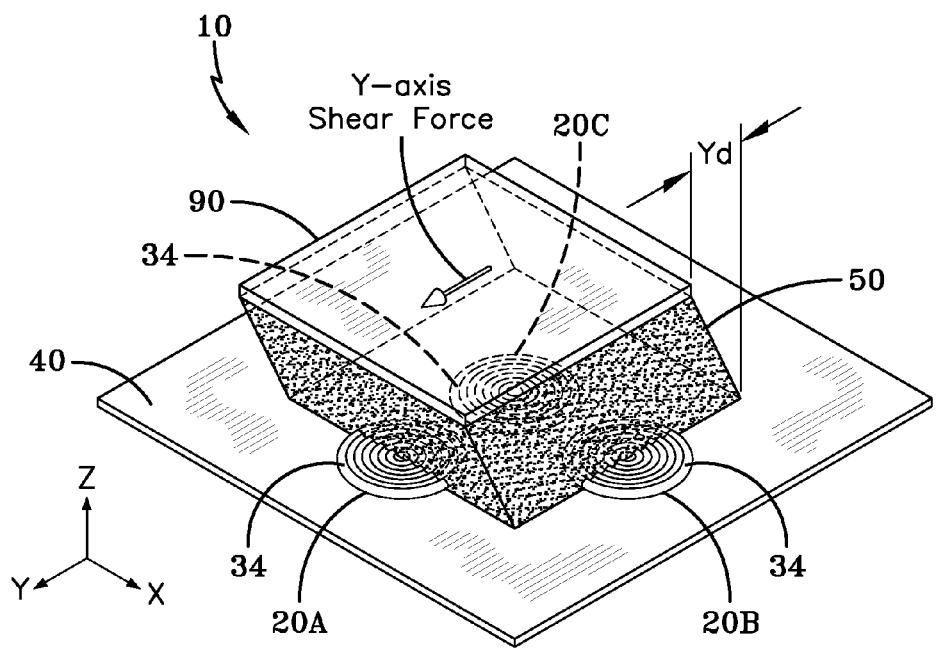
FIG. 3C is a perspective view of the wearable inductive force-sensor when a shear force is applied thereto along the y-axis in accordance with the concepts of the present invention.

Thus, the inductance change of coil 20C is related to the gap $Z_d$, shown in FIG. 3A, which is defined as the distance between the conductive plate 90 and the coil 20C. Therefore, when a normal force, such as from a foot, or from external forces applied to the foot, is applied to the outer surface of the conductive plate 90, the flexible section 50 is compressed, and the distance $Z_d$ is decreased, which leads to a decrease of the inductive $L_{s1}$ of coil 20A. Meanwhile, the displacement of the conductive member 90 along the x direction ($Z_x$), shown in FIG. 3B, and the displacement of the conductive member 90 along the y direction ($Z_y$), shown in FIG. 3C, which are caused by the application of shear forces to the sensor 10, affects the inductances $L_{s1}$ and $L_{s2}$ of coil 20A and coil 20B respectively, but does not affect $L_{s3}$ of coil 20C. Therefore, the normal force can be measured by monitoring the inductance $L_{s3}$ of coil 20C. In addition, the inductance $L_{s1}$ of coil 20A is a function of the normal force and the y-axis shear force. Once the normal force is obtained from the inductance $L_{s3}$ of coil 20C, the y-axis shear force can be identified from $L_{s1}$ of coil 20A. Similarly, the inductance $L_{s2}$ of coil 20B is a function of the normal force and the x-axis shear force, and as such, the x-axis shear force can be identified from the inductance $L_{s2}$ of the coil 20B. The manner for identifying the normal, x-axis shear force is discussed in detail below.

During operation of the sensor 10, the combined excitation signal $V_o$, which is generated by the signal generator 110, includes three separate sine waves, each having a frequency that is close to the resonant frequency of one of the LC resonance circuits 150A-C associated with respective sensing coils 20A-C to which the signal $V_o$ is applied. After the excitation signal $V_o$ is applied, only one combined response $V_{out}$, which includes the responses of the coils 20A-C when each of the 3 sine waves are applied, is required to be measured via the force data-acquisition unit 120. However, any number of sine waves may be used, depending on the number of coils used by the sensor 10. Because each individual response signal of the combined response signal that is generated from each sensing coil 20A-C exhibits a peak or maximum amplitude at its resonant frequency, the response signals for each individual coil 20A-C can be recovered or identified from a combined response signal that includes the individual responses of all of the coils 20A-C by analyzing the spectrum components at each resonant frequency using a multiplexing technique to be discussed.

That is, multiplexing is performed, such that $V_{out}$ is divided into many segments of data. Next, a Fast Fourier Transform (FFT) is performed for each segment of $V_{out}$ data, which allows for the identification of the peak values of individual voltage components at each of the three resonant frequencies. The peak values of all the time segments for each individual frequency component are then combined to obtain the individual voltage components from the sensing coils 20A-C, excluding the carrier sine wave signal. As such, the change in inductance $L_{si}$ of each sensing coil 20A-C can, therefore, be calculated from the individual response signals generated by each coil 20A-C. This is accomplished due to the relationship between the individual response signals and the inductance $L_{si}$ of the sensing coils 20A-C, which is defined by a set of non-linear equations. In one aspect, an iterative numerical method may be utilized to calculate the inductance of the coils 20A-C, whereby the approximate solutions of the inductances $L_{s1}$, $L_{s2}$ and $L_{s3}$ can be obtained using known techniques. It should also be appreciated that other techniques of resonant frequency division multiplexing may also be used by the present invention. It is also contemplated that the force detection process utilized by the present invention may be configured to monitor the pressure applied to the sensor 10 in real-time or near real-time.

The output of the inductive-force sensor 10 not only relates to the normal force and shear force, but also depends on the material and size of the target plate or conductive member 90 and the geometry of the sensing coils 20A-C. To acquire an accurate relationship between the applied force and the inductance change of the sensing coils 20A-C, a calibration process for the sensing coils 20A-C is performed at different normal forces magnitudes and shear forces magnitudes.

The calibration process is performed by first measuring a base inductance value of the sensing coils 20A-C at each resonant frequency of the coils 20A-C. Next, a normal force $F_z$ is applied along the z-direction on the conductive member 90 and is swept from about 0 to 800 N with an approximately 44N step size. At each normal force step, a shear force $F_x$ is applied along the x-direction on the conductive member 90 and this force is swept from 0 to 130N with a 44N step size. The inductance change of each sensing coil 20A-C is measured at each step at its specific excitation or resonant frequency. The changes in inductance ($\Delta L_s/L_s$) as a function of $F_z$ and $F_y$ are plotted as a calibration curve. Next, a shear force $F_y$ is applied along the y direction and is swept from 0 to 130N with a 44N step size at each normal force. Then the inductive change caused by force $F_z$ and force $F_y$ are also plotted as a calibration curve.

Figure 5A:
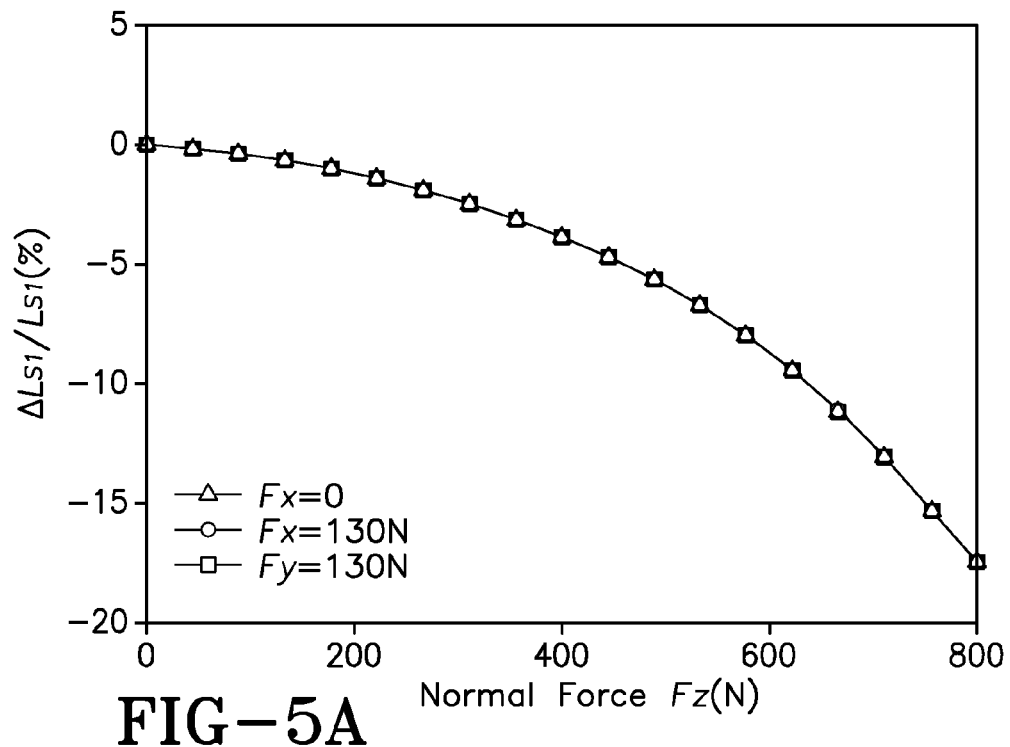
FIG. 5A is a graph showing the change in inductance of coil 20C as a function of normal force.
Figure 5B:
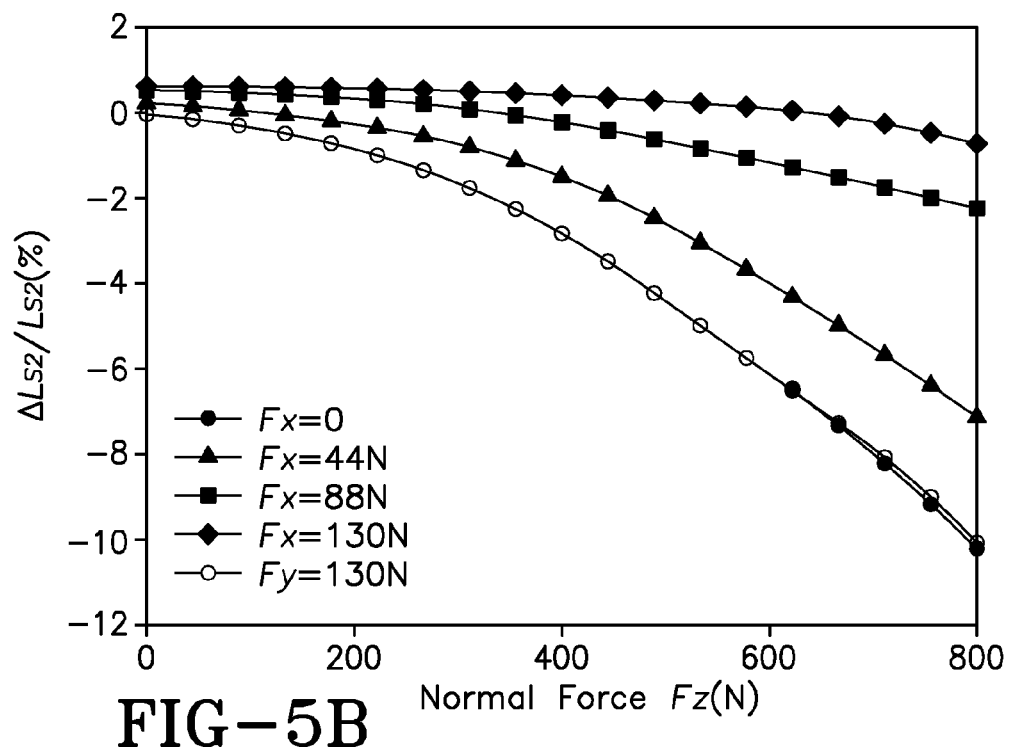
FIG. 5B is a graph showing the change in inductance of coil 20B as a function of normal force under different shear forces.
Figure 5C:
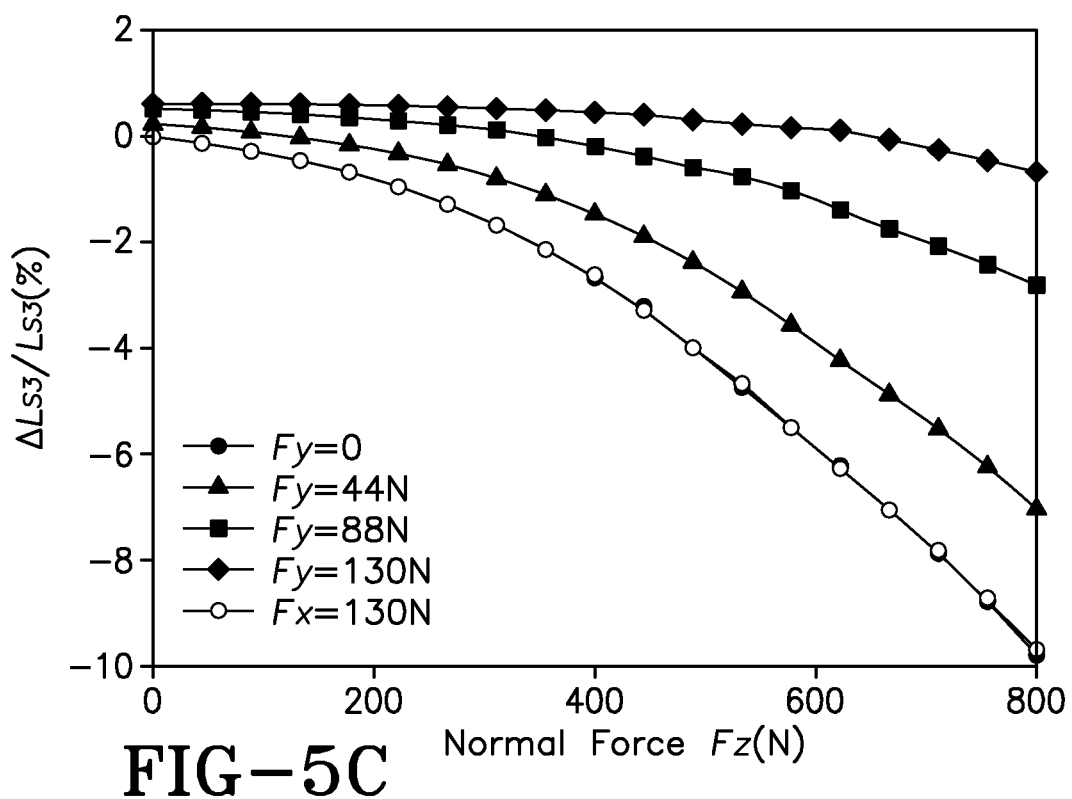
FIG. 5C is a graph showing the change in inductance of coil 20A as a function of normal force under different shear forces.

Thus, using each calibration curve, shown in FIGS. 5A-C, is obtained by five repetitive measurements. Force $F_z$ can then be determined from the response of sensing coil 20C directly and independently using the calibration curve shown in FIG. 5A without analyzing the responses from coil 20A and 20B. This is because inductance $L_{s3}$ of coil 20C is only sensitive to the normal force F. The inductance of sensing coil 20B, $L_{s2}$, is sensitive to both normal force $F_z$ and x-axis shear force $F_x$, as shown in FIG. 5B, but insensitive to y-axis shear force $F_y$. To determine the shear force $F_x$, normal force should first be determined from the response of sensing coil 20C, using calibration curve shown in FIG. 5A. Once this normal force $F_z$ has been determined, shear force $F_x$ can be determined from the calibration curve shown in FIG. 5B associated with sensing coil 20B. Similarly, shear force $F_y$ can be determined from the inductance change, $L_{s1}$, of sensing coil 20A after the normal force is determined using calibration curve, shown in FIG. 5C associated with sensing coil 20A.

In one aspect, the data embodied by the calibration curves of FIGS. 5A-C may be represented numerically and stored at the DAR 120 of the force-measurement device 100. Thus, as the change in inductance of the coils 20A-C are identified by sensor 10, such inductance changes can be converted into a force measurement in real-time or near real-time.

Therefore, one advantage of the present invention is to provide a wearable, multiplexed inductive-force sensor that is configured to be attached to, or otherwise integrated with, a shoe, such as an insole of a shoe. Another advantage of the present invention is that a multiplexed inductive-force sensor utilizes one set of force-measurement electronics to measure normal force and shear force in two directions. Still another advantage of the present invention is that a multiplexed inductive-force sensor utilizes a parallel LC resonance measurement circuit that is combined with signal multiplexing, which enables high sensitivity and high resolution. Yet another advantage of the present invention is that a multiplexed inductive-force sensor is configured to simultaneously measure the normal force and two shear forces.

Thus, it can be seen that the objects of the present invention have been satisfied by the structure and its method for use presented above. While in accordance with the Patent Statutes, only the best mode and preferred embodiment has been presented and described in detail, with it being understood that the present invention is not limited thereto or thereby. Accordingly, for an appreciation of the true scope and breadth of the invention, reference should be made to the following claims.

What is claimed is:

1. A force sensor comprising:
   a substrate;
   a first, second and third coil disposed on said substrate each adapted to generate an initial magnetic field upon receipt of an A.C. (alternating current) signal; a capacitor coupled in parallel with each one of said coils;
   an electrically conductive section supported by a section of flexible material, wherein said flexible material is attached to said substrate, such that said electrically conductive section is spaced from said coils, whereby one of said initial magnetic fields forms one or more corresponding induced magnetic fields in said electrically conductive section;
   wherein upon an application of a force to the sensor, at least one of said substrate and said electrically conductive section moves, such that a position of one or more said coils relative to said electrically conductive section is changed, whereby one or more of said induced magnetic fields are detected by one or more of said coils, so as to change a magnitude of inductance of one or more of said coils, with each said change in magnitude of inductance being associated with a measurement of the application of force; and
   wherein said electrically conductive section has an edge that passes through a center of said first and second coils.

2. The force sensor of claim 1, further comprising an insole of a shoe that includes said coils.

3. The force sensor of claim 1, wherein said substrate comprises a dielectric material.

4. The force sensor of claim 1, wherein said coils comprise spiral-wound coils.

5. The force sensor of claim 4, wherein said spiral-wound coils comprise planar coils.

6. The force sensor of claim 5, wherein said spiral-wound planar coils comprise a plurality of turns.

7. The force sensor of claim 1, wherein said section of flexible material is formed of rubber.

8. The force sensor of claim 1, wherein said electrically conductive section comprises stainless steel.

9. The force sensor of claim 1, further comprising:
   a force-measurement device coupled to said first, second and third coils, wherein said force-measurement device is configured to measure an amount of movement of said electrically conductive section relative to said coils, so as to calculate therefrom the measurement of the application of the force.

10. The force sensor of claim 9, wherein said force-measurement device comprises:
    a resistor coupled in series with said first, second and third coils;
    an A.C. (alternating current) signal generator that is coupled in series with said resistor; and a data acquisition unit coupled in parallel with said first, second and third coils;

wherein said A.C. signal generator generates a combined signal, which includes a plurality of signals each having a resonant frequency associated with said first, second and third coils respectively, such that said data acquisition unit monitors said first, second and third coils to identify the amount of force applied to the sensor.

11. The force sensor of claim 9, wherein said force-measurement device includes a communication interface to transfer the calculated amount of force to a remote computer.

12. The force sensor of claim 9, wherein said force-measurement device calculates the amount of force in real-time.

13. The force sensor of claim 1, further comprising:
a controller configured to identify the change in magnitude of said magnetic field of one or more of said coils to generate therefrom a measurement of one or more forces applied to the sensor.

14. The force sensor of claim 1, wherein said electrically conductive section covers said third coil.

15. The force sensor of claim 1, wherein said substrate comprises an insole.

16. The force sensor comprising: a substrate; a first, second and third coil disposed on said substrate each adapted to generate an initial magnetic field upon receipt of an A.C. (alternating current) signal;

a capacitor coupled in parallel with each one of said coils;

an electrically conductive section supported by a section of flexible material, wherein said flexible material is attached to said substrate, such that said electrically conductive section is spaced from said coils, whereby one of said initial magnetic fields forms one or more corresponding induced magnetic fields in said electrically conductive section, and wherein said section of flexible material comprises a plurality of individual sections of flexible material; and a cover plate that is supported by said plurality of individual sections of flexible material, with said electrically conductive section being attached to said cover plate, wherein upon an application of a force to the sensor, at least one of said substrate and said electrically conductive section moves, such that a position of one or more said coils relative to said electrically conductive section is changed, whereby one or more of said induced magnetic fields are detected by one or more of said coils, so as to change a magnitude of inductance of one or more of said coils, with each said change in magnitude of inductance being associated with a measurement of the application of force.

* * * * *